United States Patent
Wolinsky et al.

(10) Patent No.: US 6,840,956 B1
(45) Date of Patent: Jan. 11, 2005

(54) SYSTEMS AND METHODS FOR DEPLOYING A BIOSENSOR WITH A STENT GRAFT

(75) Inventors: Lone Wolinsky, Ramat Gan (IL); Avi Penner, Tel Aviv (IL)

(73) Assignee: Remon Medical Technologies LTD, Caesarea (IL)

( * ) Notice: Subject to any disclaimer, the term of this patent is extended or adjusted under 35 U.S.C. 154(b) by 0 days.

(21) Appl. No.: 09/522,724

(22) Filed: Mar. 10, 2000

(51) Int. Cl.[7] ................................................. A61B 5/02
(52) U.S. Cl. ...................... 623/1.13; 600/454; 600/505
(58) Field of Search ............................ 623/1.11, 1.12, 623/1.13, 1.14, 1.15, 1.16, 1.17, 1.18, 1.19, 1.2, 1.21; 606/191, 194, 195, 198; 600/505, 454

(56) References Cited

U.S. PATENT DOCUMENTS

| | | | | |
|---|---|---|---|---|
| 5,040,538 A | * | 8/1991 | Mortazavi | 600/333 |
| 5,662,711 A | * | 9/1997 | Douglas | 604/9 |
| 5,967,986 A | * | 10/1999 | Cimochowski et al. | 600/454 |
| 6,159,156 A | * | 12/2000 | Van Bockel | 600/485 |
| 6,416,474 B1 | * | 7/2002 | Penner et al. | 600/309 |
| 6,475,170 B1 | * | 11/2002 | Doron et al. | 600/587 |

FOREIGN PATENT DOCUMENTS

WO     WO83/03348 A1     10/1983

* cited by examiner

Primary Examiner—Vy Bui
(74) Attorney, Agent, or Firm—Bingham McCutchen LLP

(57) ABSTRACT

A stent graft includes a tubular prosthetic graft, a support structure expandable between contracted and enlarged conditions, and a biosensor attached thereto. The biosensor may be directly attached to an outer surface of the graft, to struts defining the support structure, or by one or more filaments configured to dispose the biosensor beyond an outer surface of the stent graft. When the biosensor is attached by one or more filaments, the stent graft is mounted in a contracted profile on a delivery apparatus with the biosensor disposed adjacent to the stent graft thereon. The stent graft is introduced into a blood vessel in the contracted profile, and advanced endolumenally until it is positioned across an aneurysm. The stent graft is expanded towards an enlarged profile such that ends of the stent graft engage healthy regions of the vessel adjacent to the aneurysm, thereby isolating the aneurysm from the rest of the vessel with the biosensor disposed within the aneurysmal sac, the biosensor allowing remote monitoring of pressure or other conditions to detect an endoleak or excessive pressure therein.

8 Claims, 5 Drawing Sheets

# SYSTEMS AND METHODS FOR DEPLOYING A BIOSENSOR WITH A STENT GRAFT

DESCRIPTION

1. Field of the Invention

The present invention relates generally to implantable medical devices for monitoring internal physiological conditions of a patient, and, more particularly, to a stent graft having a biosensor attached thereto for remotely monitoring physiological conditions of a patient, such as pressure within an aneurysm cavity across which the stent graft is implanted.

2. Background

An aneurysm is a weakening of a wall of a blood vessel that generally results in a ballooning of the wall, and, if left untreated, may result in a rupture that may seriously threaten the life of a patient. The weakening of the wall may be due to injury, infection, or other conditions, such as a congenital defect in the arterial connective tissue. Common forms of such an aneurysm include an abdominal aortic aneurysm ("AAA"), an iliac aneurysm, a bifurcated aneurysm of the abdominal aorta and one or both of the iliac arteries, and a thoracic aortic aneurysm.

To treat a patient suffering from an aneurysm, a tubular prosthetic graft may be implanted across the aneurysm using an open surgical technique to substantially isolate the weakened region of the vessel from adjacent healthy regions. For example, the vessel wall may be cut longitudinally along the vessel wall, the graft inserted and anastomosed coaxially within the vessel as an internal replacement for the diseased segment, and then the longitudinal cut may be sutured closed. Alternatively, opposite ends of a prosthetic graft may be sutured to a vessel on either side of the weakened region to form a bypass conduit around the diseased segment. Such surgical approaches, however, may involve extensive recovery times, may be complicated because of the difficulties in suturing the graft to the vessel, and/or may be unsuitable for many at-risk patients because of the high mortality and morbidity rates associated with a surgical intervention of this magnitude.

As an alternative to open surgery, endolumenal stent graft implantation has been suggested. An endolumenal stent graft generally includes a vascular graft and a support structure, such as a self-expanding or balloon-expandable stent, that may engage each end of the graft or may extend over all or a portion of a length of the graft. The stent graft may be introduced percutaneously into the patient's vasculature in a reduced profile, for example, on or in a delivery catheter. The stent graft may be advanced to a treatment site, such as a damaged segment of the abdominal aorta, and placed across the treatment site. The support structure may then be radially expanded, anchoring the graft to the healthy regions of the vessel adjacent the damaged segment, and substantially sealing the aneurysm from the rest of the circulatory system. As a result, pressure within the isolated aneurysmal sac may be reduced, thereby reducing stress or "endotension" on the weakened wall of the vessel. Endotension is a physical parameter that may indicate the likelihood of an aneurysm rupturing, and is generally defined in terms of the internal pressure within the aneurysm, the aneurysm diameter and vessel wall thickness.

One potential complication that may occur after a stent graft is implanted is the formation of an endoleak. Endoleaks may be divided into four categories: leakage due to improper sealing of the graft against the vessel wall (Type I), blood flow into the aneurysmal sac through bypass arteries (Type II), leakage due to mechanical failure of the graft system (Type III), and leakage through the graft wall due to porosity of the graft material (Type IV).

If fluid leaks into the aneurysmal sac, it may increase the pressure or endotension within the aneurysm, possibly resulting in an aneurysmal rupture. To substantially reduce the risk of this occurring, early detection of endoleaks or endotension may be important. With early detection, the pressure within the aneurysmal sac may be reduced by subsequent endovascular treatment (for example, further expansion of the stent graft support structure, or additional stent graft implantation to improve sealing), or, if necessary, surgical intervention.

Currently, contrast-enhanced computerized tomography (CT) is often used to detect endoleaks, which relies on x-ray imaging of an abdominal region after injection of a contrast media. If an endoleak is present, the aneurysmal sac may fill with contrast media and the endoleak may then be identified by the CT scan. Although CT scans are considered a reliable method for detecting endoleaks, they require an experienced operator and an expensive apparatus, placing significant financial constraints on its frequency of use. In addition, a CT scan procedure exposes the patient to x-ray radiation, and thus may only be recommended every 3 to 6 months following stent graft implantation. Finally, because CT scans only detect actual leakage and not pressure within the aneurysm, they may not detect small leaks that may cause slow, but potentially dangerous, pressurization within the aneurysm.

As an alternative to CT scans, ultrasound imaging may be used to detect endoleaks. Ultrasound imaging uses a simpler apparatus, resulting in a potential cost savings over CT scanning, and does not involve the use of ionizing radiation and its associated risks. The quality of ultrasound imaging, however, may be more operator dependent, and therefore may be less reliable than CT scans.

Accordingly, it is believed that a system and method for monitoring internal pressure within an aneurysmal sac may be considered useful.

SUMMARY OF THE INVENTION

The present invention is directed to a stent graft having a biosensor attached thereto, and to systems and methods for implanting such a stent graft.

In accordance with a first aspect of the invention, a stent graft is provided that includes a tubular prosthetic graft, a support structure expandable between a contracted condition for facilitating introduction into a blood vessel, and an enlarged condition for substantially securing the graft across a weakened region of the blood vessel, and a biosensor attached to at least one of the graft and the support structure.

The biosensor may be directly attached to an outer surface of the graft, for example, by sutures or an adhesive, or directly to struts defining the support structure. Alternatively, the biosensor may be attached to the graft or the support structure by one or more filaments, preferably configured to dispose the biosensor beyond an outer surface of the stent graft.

The stent graft may be implanted within a target treatment site, such as an aneurysm within the abdominal aorta, using an apparatus that includes a catheter having a proximal end and a distal end adapted for introduction into a blood vessel. The distal end may include a distal region for receiving the stent graft in a contracted condition thereon.

Where the biosensor is attached to the stent graft by one or more filaments, the biosensor is preferably disposed adjacent to the stent graft on the catheter. In some preferred embodiments, a constraint may secure the stent graft and/or biosensor to the distal region of the catheter, such as a retractable sheath that may be slidable between an extended position covering the stent graft and a retracted position wherein the stent graft is exposed.

The implantation catheter preferably includes a tapered nose portion on the distal end that defines a cavity for receiving the biosensor therein when the stent graft is received on the distal region. The sheath preferably includes a tongue or other flexible member extending distally from its distal end, the tongue being configured to extend into the cavity of the tapered nose portion when the sheath is disposed in its extended position, thereby substantially securing the biosensor within the cavity.

The stent graft may be provided in a contracted profile state on the delivery apparatus, which may then be percutaneously introduced into a patient's vasculature. The stent graft may be advanced endolumenally until it is positioned across an enlarged weakened region of an aneurysm or other treatment site. The stent graft may then be expanded from the contracted profile towards an expanded profile such that ends of the stent graft engage healthy regions adjacent the weakened region.

Thus, the stent graft may substantially isolate a cavity defined by the enlarged weakened region from the rest of the blood vessel, with the biosensor disposed within the cavity. The biosensor may then be used to remotely monitor physiological conditions within the cavity, such as pressure, to detect potential problems, such as an endoleak or excessive pressure within the cavity that may further damage the treatment site. If a problem is detected, the patient may receive additional treatment before the problem results in a serious or life-threatening condition, such as an aneurysmal rupture.

Other objects and features of the present invention will become apparent from consideration of the following description taken in conjunction with the accompanying drawings.

BRIEF DESCRIPTION OF THE DRAWINGS

Preferred embodiments of the present invention are illustrated by way of example, and not by way of limitation, in the figures of the accompanying drawings, in which like reference numerals refer to like components, and in which.

DETAILED DESCRIPTION OF THE PREFERRED EMBODIMENTS

Figure 1:
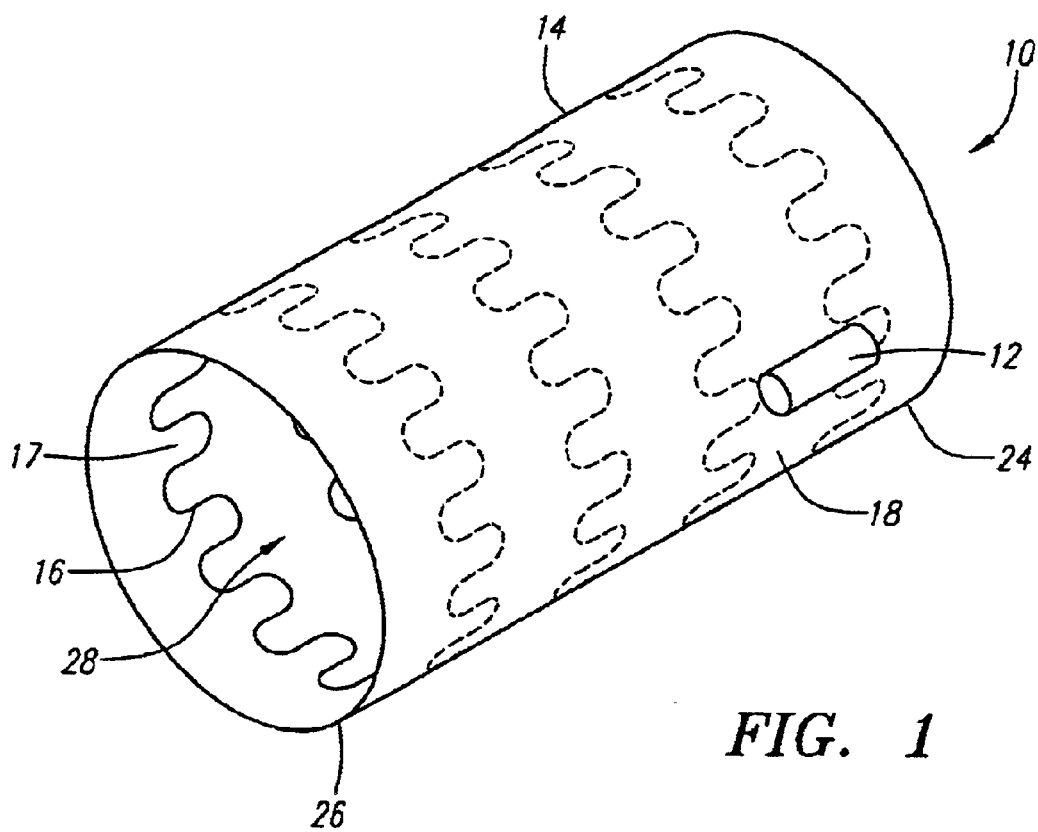
FIG. 1 is a perspective view of a first preferred embodiment of a stent graft having a biosensor attached to an outer surface thereof.

Turning now to the drawings, FIG. 1 shows a first preferred embodiment of a stent graft 10 with an attached biosensor 12, in accordance with the present invention. The stent graft 10 generally includes a tubular prosthetic graft 14, and a support structure 16 attached to the graft 14. The graft 14 may be provided from a substantially non-porous biocompatible material, such as Dacron or ePTFE, that is formed into a tubular shape. The material is substantially flexible, thereby allowing the graft 14 to be rolled or folded into a reduced profile, accommodating delivery through tortuous anatomy, and/or facilitating implantation within curved blood vessels.

The support structure 16 is preferably a tubular stent that extends along an inside surface 17 of the graft 14 for substantially the entire length of the graft 14. The support structure 16 may be attached to the graft 14 in a variety of ways, such as by sutures, wires, sonic welding, adhesives, and the like, as is well known in the art. In an alternative embodiment, the support structure 16 may be attached to an outer surface 18 of the graft (not shown), or may be woven into the graft material (also not shown). In a further alternative, a pair of stents (not shown) may be provided that may be attached to respective end regions of the graft 14, with an intermediate region of the graft 14 being unsupported.

The support structure 16 is radially expandable between a contracted condition for facilitating introduction into a patient's vasculature, and an enlarged condition for substantially engaging the wall of a blood vessel. In one embodiment, the support structure 16 may be a self-expanding stent, i.e., that is biased towards its enlarged condition but may be compressed and/or constrained in its contracted condition during delivery. Alternatively, the support structure 16 may be a plastically-deformable stent, i.e., that remains in its contracted condition until it is forcibly expanded to assume its enlarged condition, for example, using a balloon.

The biosensor 12 is directly attached to an outer surface 18 of the graft 14, for example, by sutures or an adhesive. Alternatively, the biosensor 12 may be received in a pocket (not shown) or otherwise secured within the material of the graft 14. The biosensor 12 may be mounted at a predetermined location on the stent graft 10, for example, adjacent to one end 24 thereof. Alternatively, a plurality of biosensors 12 may be provided (not shown) at various locations along the length and/or around the circumference of the stent graft 10.

The biosensor 12 may be one of a variety of known sensors for remotely monitoring physiological parameters of a patient, such as a pressure sensor, a temperature sensor, a pH sensor, a blood sugar sensor, a blood oxygen sensor, a motion sensor, a flow sensor, a velocity sensor, an acceleration sensor, a force sensor, a strain sensor, an acoustics sensor, a moisture sensor, an osmolarity sensor, a light sensor, a turbidity sensor, a radiation sensor, an electromagnetic field sensor, a chemical sensor, an ionic sensor, and an enzymatic sensor.

In preferred embodiments, the biosensor 12 includes at least a pressure monitoring sensor ("PMS") that may be used to monitor pressure within an aneurysmal cavity, as described further below. Also, the biosensor 12 preferably employs wireless telemetry to deliver information from the implantation site to an instrument external to the body. Further, the biosensor may or may not require a battery.

For example, one preferred biosensor 12 is constructed in accordance with the teachings of U.S. patent application Ser. No. 09/303,644, which is fully incorporated by reference for all that it teaches and discloses. As taught therein, an acoustic telemetry biosensor includes means for converting acoustic energy received from an externally originated interrogation signal into a current supply for powering one or more sensors embedded in the biosensor for measuring various biological parameters at the implantation site. The biosensor further includes means for modulating the interrogation signal to transmit the measured information external to the body.

In another preferred embodiment, the biosensor 12 is constructed in accordance with the teachings of U.S. Pat. No. 5,704,352, which is also fully incorporated by reference for all that it teaches and discloses. Other biosensor constructions are also possible and will be known to those skilled in the art.

Figure 2:
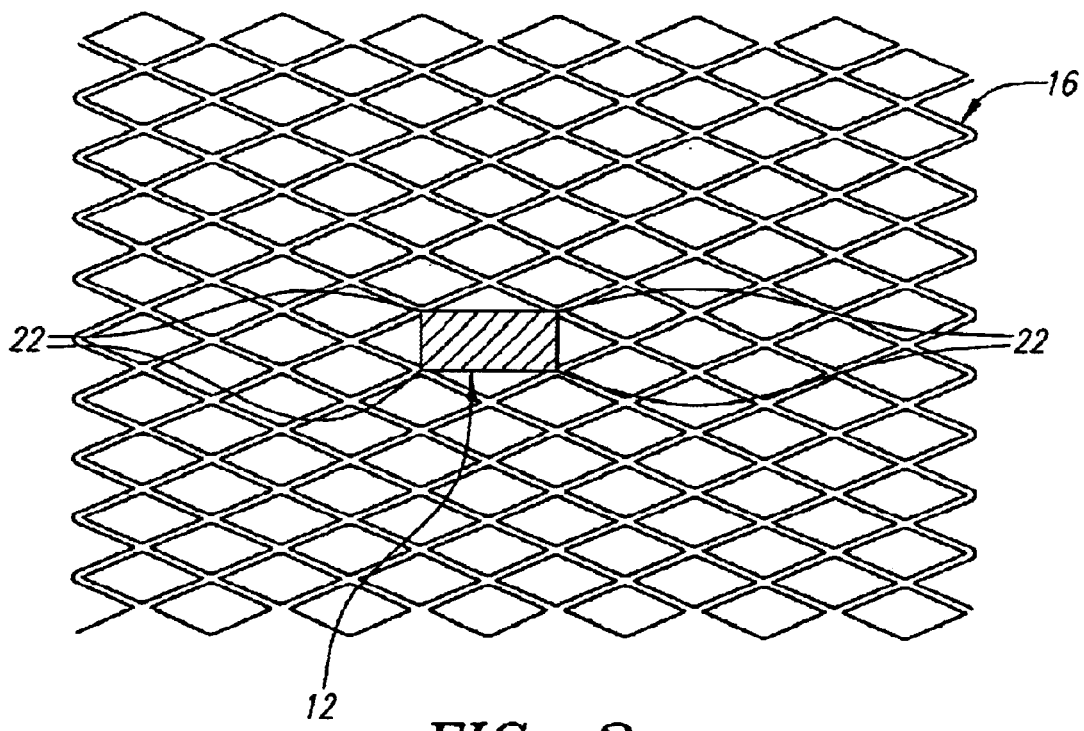
FIG. 2 is a top view of an unrolled stent structure to which a biosensor is attached.

Turning to FIG. 2, in an alternative embodiment, the biosensor 12 may be attached within the support structure 16, possibly reducing the profile of the resulting stent graft 10. In this embodiment, one or more individual struts may be removed from the support structure 16 to accommodate insertion of the biosensor 12 therein. The biosensor 12 may then be placed within the resulting space and attached to the adjacent struts 22, for example, by sutures, adhesives or sonic welding. Because the biosensor 12 is attached to the support structure 16, the support structure 16 is preferably attached to the outer surface of the graft 14 to expose the biosensor 12 outside the resulting stent graft 10.

Alternatively, a "hole" shaped similar to the biosensor 12 may be cut or otherwise provided in the graft material if the support structure 16 is attached to the inner surface of the graft 14. The perimeter of the hole may be sealed against the biosensor 12, thereby exposing the biosensor 12 to the outside of the stent graft 10.

Figure 3A:
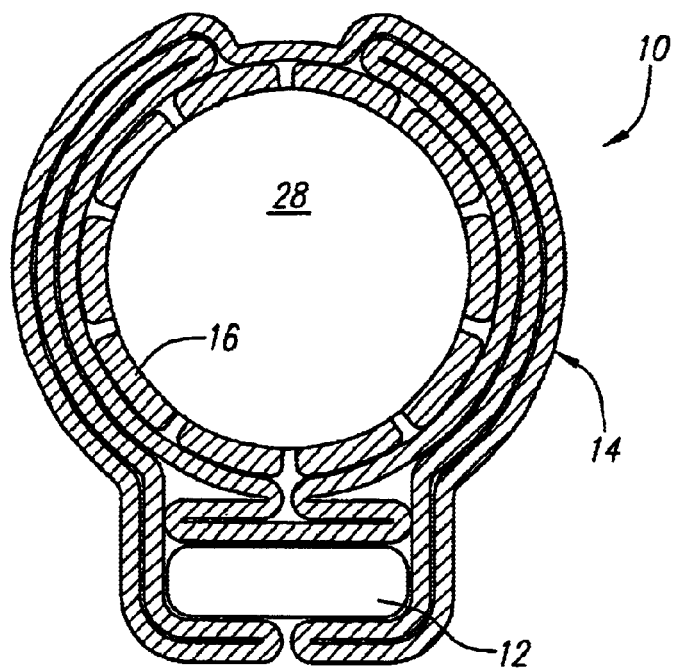
FIGS. 3A and 3B are cross-sectional end views of alternative embodiments of a stent graft folded into a contracted condition, the stent graft having a biosensor attached to its outer surface.
Figure 3B:
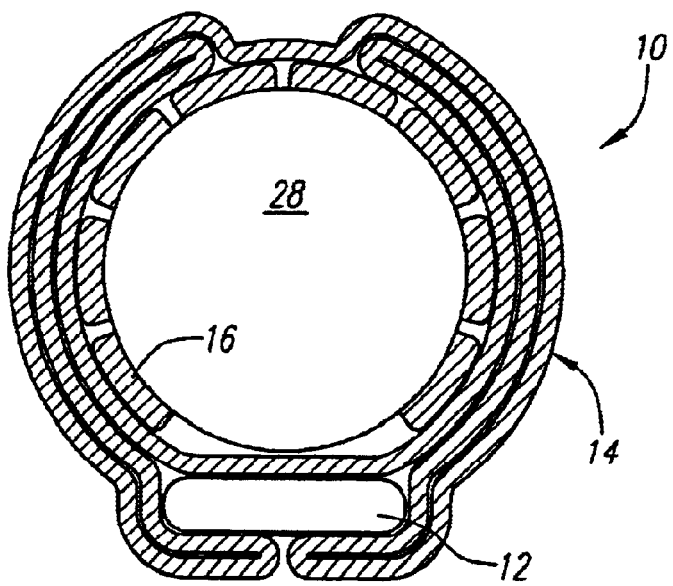

Turning to FIGS. 3A and 3B, the support structure 16 is initially provided in a contracted condition, for example, having a cross-section or diameter of about 3–8 mm. The graft 14 is rolled or folded around the support structure 16, thereby providing the stent graft 10 in a reduced profile state for delivery to a target treatment site. The biosensor 12 is placed if within the folds of the graft 14 in order to protect the biosensor during delivery. The support structure 16 may be expandable to an enlarged condition having a cross-section or diameter that is several times larger than the contracted condition, e.g., between about 7–30 mm. In the enlarged condition, the graft 14 is substantially supported in an open tubular shape by the support structure 16, thereby defining a lumen 28 extending through the stent graft 10.

Figure 4A:
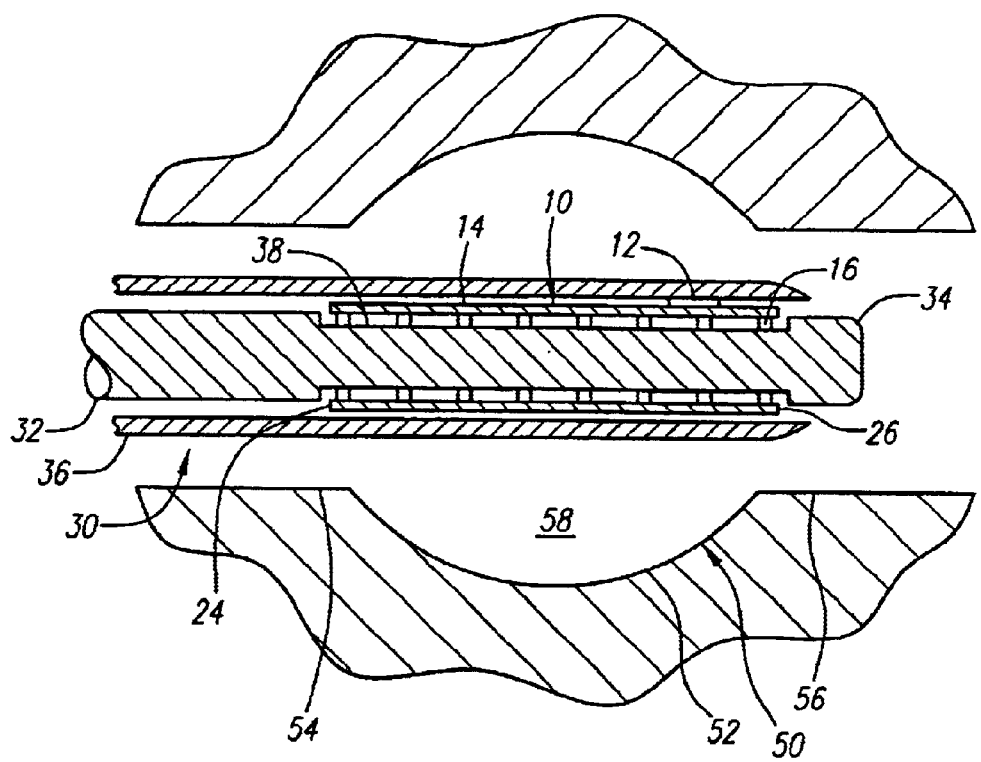
FIGS. 4A and 4B are cross-sectional views of an aneurysm site, showing delivery thereto of a stent graft having a biosensor attached directly to an outer surface thereof.
Figure 4B:
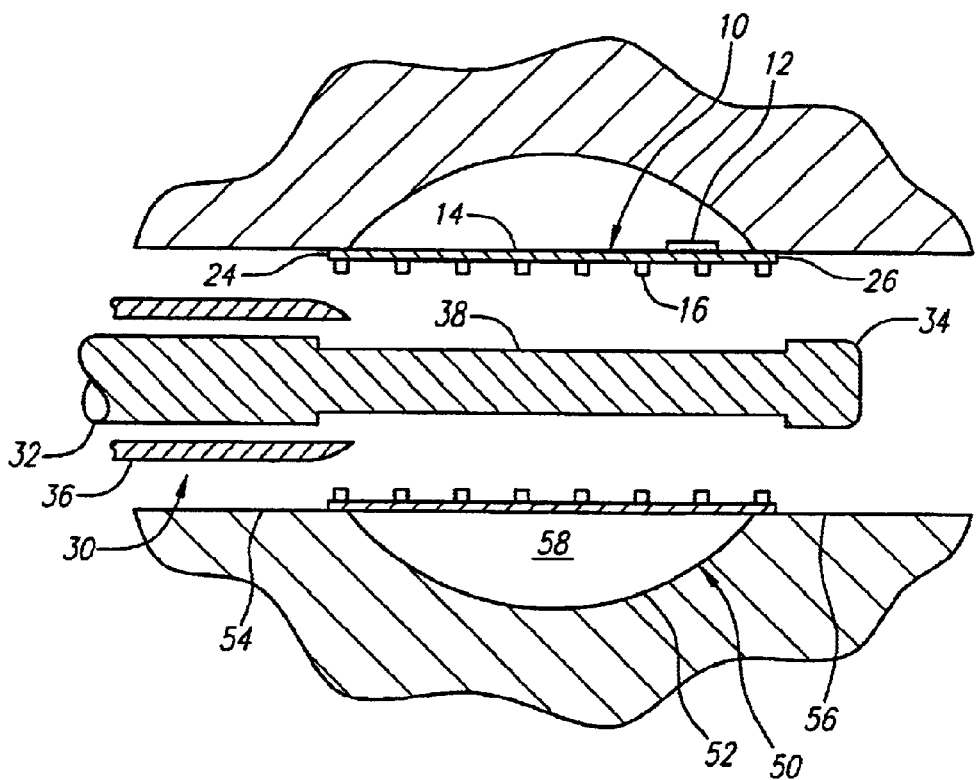

Turning to FIGS. 4A and 4B, the stent graft 10 may be mounted on a delivery device 30 for introduction and delivery into a patient's vasculature. The delivery device 30 generally includes a catheter 32 having a proximal end (not shown) and a distal end 34 having a size and shape to facilitate insertion into a blood vessel. A retractable sheath 36 is slidable over the catheter 32 for covering and exposing a distal region 38 of the catheter 32.

The stent graft 10 may be placed on the distal region 38 of the catheter 32 in its reduced profile state, or alternatively, the stent graft 10 may be placed on the distal region 38 and then contracted to its reduced profile state. The sheath 36 may then be advanced over the distal region 38, thereby constraining the stent graft 10 in its reduced profile state, for example, if the support structure is self-expanding, and/or protecting the stent graft 10 during delivery.

The distal end 34 of the catheter 32 may then be introduced into a patient's vasculature, for example, percutaneously into a peripheral vessel, such as a iliac artery, and advanced endolumenally until a treatment site 50 is reached. In a preferred embodiment, the treatment site 50 is an aneurysm within the abdominal aorta, although other aneurysms, diseased vessels, occluded regions, and the like may also be treated. By way of example, the treatment site may also be a region of the cranial artery.

The stent graft 10 may be positioned across the treatment site 50, for example, such that the stent graft 10 spans an enlarged weakened region 52 between two healthy regions 54, 56. The positioning of the stent graft 10 may be facilitated by fluoroscopy, i.e., externally imaging radiopaque markers (not shown), as is known in the art.

The stent graft 10 may then be deployed at the treatment site 50, for example, by retracting the sheath 36 to expose the stent graft 10 within the treatment site 50. The stent graft 10 may be expanded until ends 24,26 of the stent graft 10 engage the respective healthy regions 54, 56 of the treatment site 50. Thus, the stent graft 10 may substantially isolate the cavity 58 defined by the enlarged weakened region 52 from the rest of the blood vessel.

In one embodiment, the support structure 16 may be self expanding, and therefore the stent graft 10 may automatically expand towards its enlarged condition when the sheath 36 is withdrawn. Alternatively, the support structure 16 may be plastically deformable, and therefore may require an expandable member, such as a balloon, to forcibly expand the support structure 16. For this latter embodiment, a balloon (not shown) may be provided on the distal region 38 of the catheter 32 over which the stent graft 10 is mounted. Otherwise, a balloon may be provided on the catheter 32 adjacent to the distal region 38 (not shown), or may be provided on a separate balloon catheter (also not shown) that may be subsequently introduced into the treatment site 50 after deployment of the stent graft 10. The balloon may be expanded to plastically deform the support structure 16 radially outward until it substantially engages the healthy regions 54, 56 of the treatment site 50, and then subsequently deflated and withdrawn.

When the stent graft 10 is implanted across the treatment site 50, the biosensor 12 is preferably disposed within the cavity 58. Thus, the biosensor 12 may then be used to monitor physiological conditions of the patient, such as pressure within the cavity 58, after implantation of the stent graft 10. The biosensor 12 may be activated remotely to provide pressure or other data, and thereby facilitate monitoring the condition of an aneurysm to detect early signs of leaks or other potential problems.

Figure 5A:
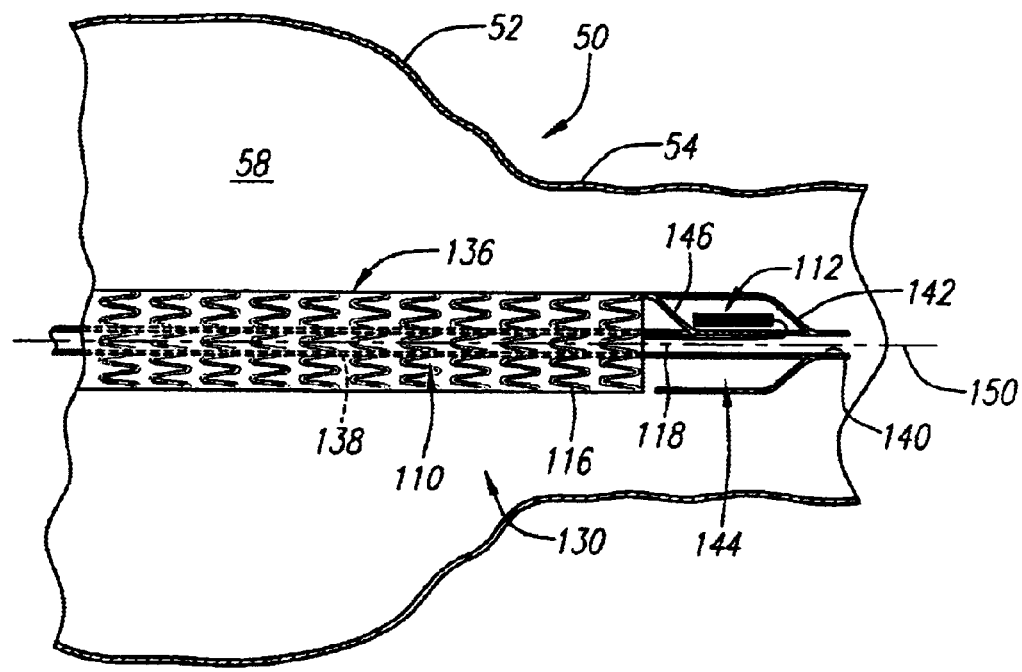
FIGS. 5A and 5B are cross-sectional views of an aneurysm site, showing the delivery thereto of a stent graft having a biosensor tethered to the stent graft by a single filament.
Figure 5B:
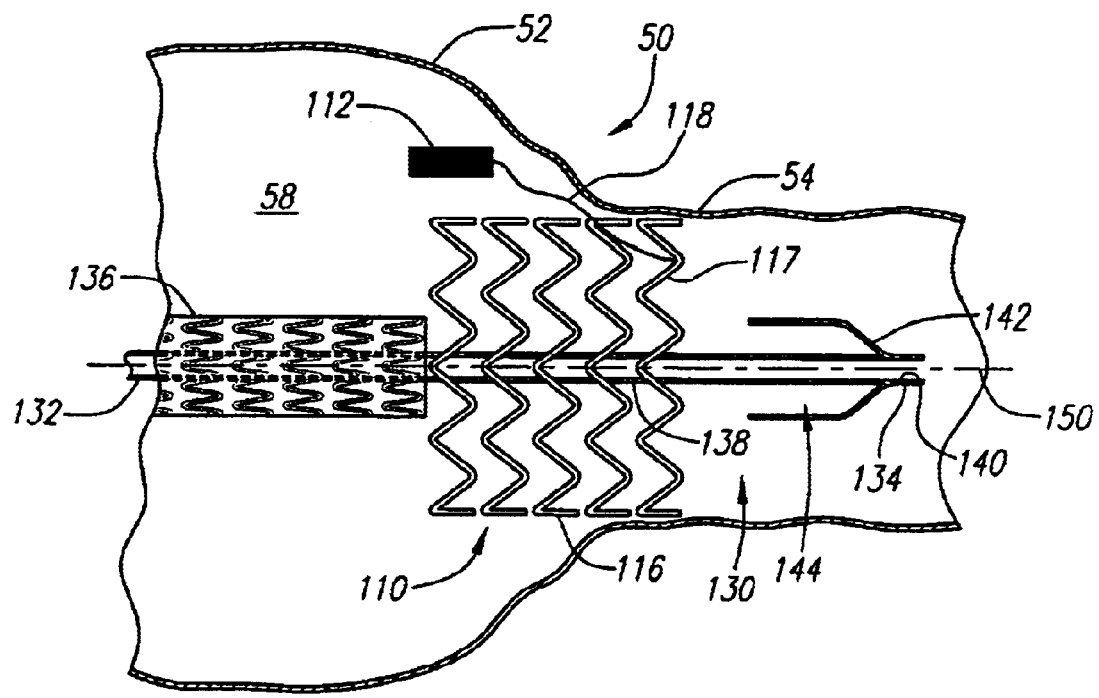

Turning to FIGS. 5A and 5B, a second preferred embodiment of a stent graft 110 is shown that includes a tubular prosthetic graft (not shown for clarity) attached to a support structure 116, similar to the embodiments described above. A biosensor 112 is tethered to the stent graft 110 by a filament 118, preferably attached to an outer surface of the stent graft 110. The filament 118 may be attached to the stent graft 110 by stitching or tying it to a predetermined location on the graft or to one of the struts 122 defining the support structure, although an adhesive may also be used. The filament 118 may reduce the profile of the stent graft 110, because the biosensor 112 is not directly attached to the stent graft 110, yet may limit movement of the biosensor 112 relative to the stent graft 110.

Alternatively, the biosensor 112 may be attached to the stent graft 110 by a sling or harness (not shown) that may be engaged around the biosensor 112 and attached to a predetermined location on the stent graft 110. In a further alternative, the filament 118, sling or harness may be attached to a loop or sleeve (not shown) that extends around a circumference of the stent graft 110. The loop or sleeve may be fixed to the stent graft 110 or may be slidable along a portion of the length thereof.

In addition, the loop or sleeve may be formed from an elastic material, such that it may substantially engage an outer surface of the stent graft 110 both in its reduced profile state and in its enlarged state. The elasticity of this latter embodiment is preferably sufficiently strong to secure the biosensor 112 to the stent graft 110, yet prevent the loop or sleeve from constricting the stent graft 110, particularly in the enlarged state.

A delivery device 130 may be provided for delivering the stent graft 110 that generally includes a catheter 132 and a sheath 136. The catheter 132 is a flexible elongate member including a proximal end (not shown), a distal end 134 having a size and shape to facilitate introduction into a patient's vasculature, and a guidewire lumen 140 extending between the proximal and distal ends 134.

A tapered nose portion 142 extends proximally from the distal end 134 of the catheter 132, thereby defining a cavity 144 for receiving the biosensor 112. The sheath 136 is a generally tubular body having a flexible tongue 146 or other flexible member extending distally from its distal end 148.

The stent graft 110, in its reduced profile state, may be mounted on a distal region 138 of the catheter 132 adjacent the tapered nose portion 142 with the biosensor 112 placed within the cavity 144. The sheath 136 may then be advanced over the stent graft 110 until the stent graft 110 is substantially covered, and the tongue enters the cavity 144. As the sheath 136 is advanced, the tongue 146 may slidably engage the filament 118 between the tongue 146 and the catheter 132, and pass under the biosensor 112, thereby substantially securing the biosensor 112 within the cavity 144. The distal end 148 of the sheath 136 preferably then engages the tapered nose portion 142, thereby providing a substantially smooth outer surface for the delivery device 130.

Because the biosensor 112 is mounted adjacent the to stent graft 110 on the catheter 132, the profile of the delivery device 130 may be reduced, thereby facilitating its introduction into a patient's vasculature. For example, the delivery device 130 may have a cross-section as small as 10–12 French.

The delivery device 130, with the stent graft 110 therein, may be percutaneously introduced into a patient's vasculature, and advanced to a target treatment site 50, for example, over a guidewire 150 already placed across the treatment site 50 using known methods. The stent graft 110 may be positioned across an enlarged weakened region 52 of the treatment site 50 and deployed, as described above.

FIG. 5B shows a stent graft 110 having a self-expanding support structure 116 including a plurality of substantially independently self-expanding cells or rings 117. As the sheath 136 is withdrawn, the tongue 146 releases the biosensor 112, and then the distal-most cells 117 may automatically expand. Because the filament 118 is attached to one of these distal cells 117, the biosensor 112 may be pulled out of the tapered nose portion 142 and into the cavity 58 defined by the enlarged weakened region 52, where it may then be used to monitor conditions within the cavity 158. To substantially reduce the risk of the biosensor 112 catching or snagging on the stent graft 110 or within the treatment site 50, the biosensor 112 may be coated with a substantially smooth layer of bio-compatible polymer, for example, of 50 microns or more thickness, such as silicon, epoxy, polyurethane, and the like.

Once the sheath 136 is fully retracted, the stent graft 110 may expand to substantially engage the healthy regions 54, 56 adjacent the weakened region, thereby substantially isolating the cavity 58. If the stent graft 110 is balloon-expandable, a balloon (not shown) may be provided on the distal region 138 of the catheter 132 that may be inflated to expand the stent graft 110 to its enlarged profile. A filament 118 is used to attach the biosensor 112 to the stent graft 110 and to position the biosensor 112 within the cavity 58. The delivery system 130 may then be withdrawn, leaving the stent graft 110 in place, and the biosensor 112 within the cavity 58 for monitoring one or more physiological conditions therein.

Figure 6A:
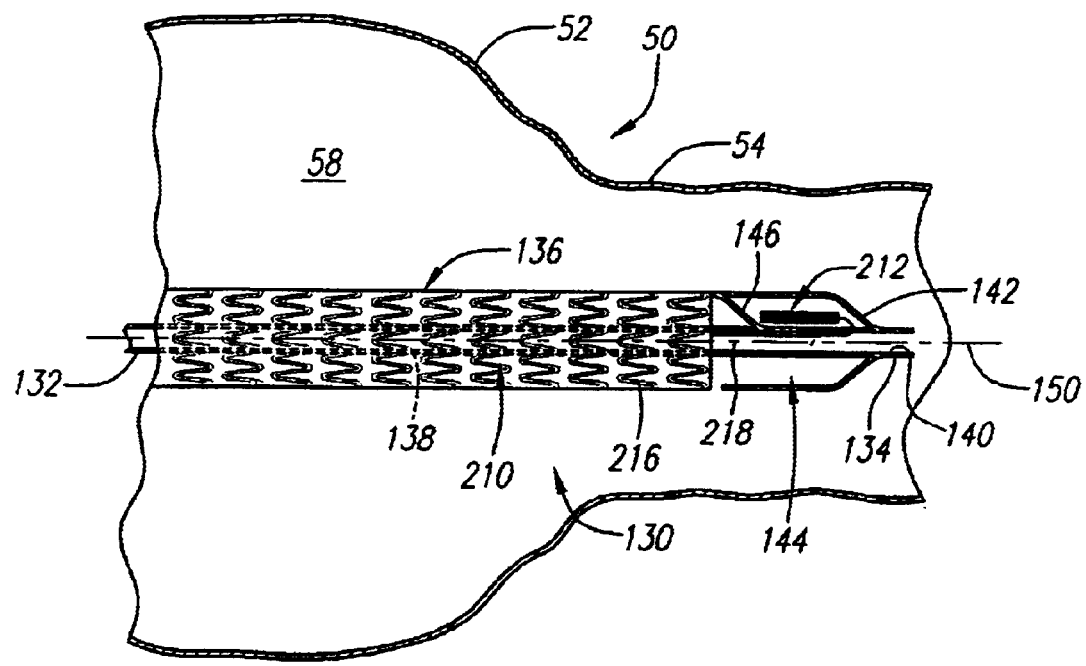
FIGS. 6A and 6B are cross-sectional views of an aneurysm site, showing the delivery thereto of a stent graft having a biosensor tethered to the stent graft by a pair of filaments.
Figure 6B:
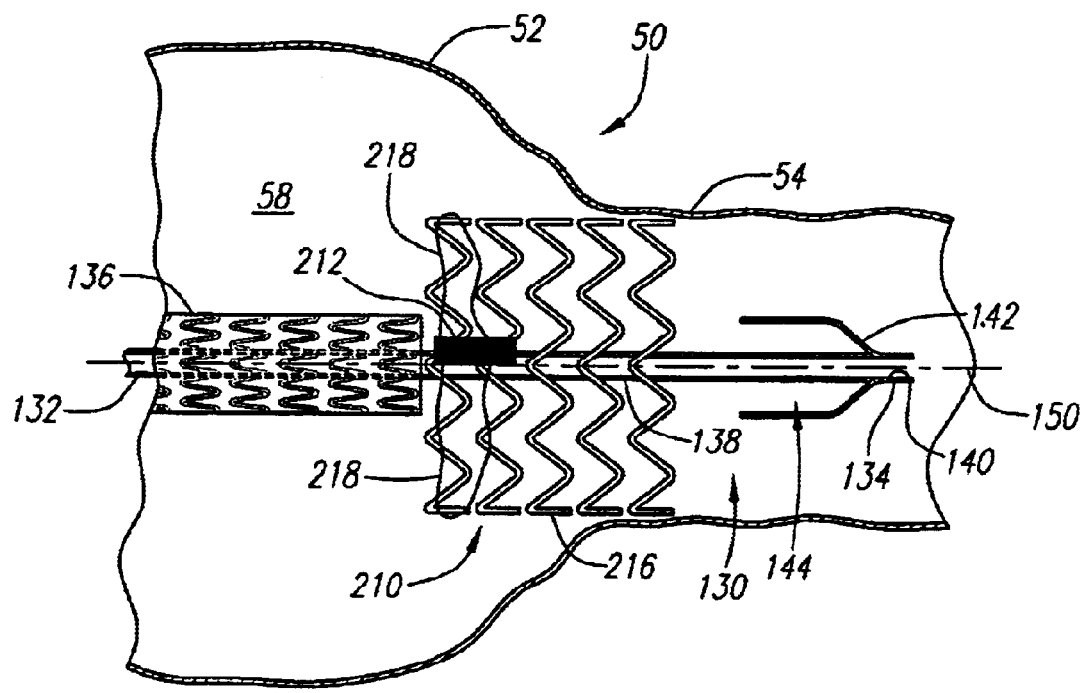

Turning to FIGS. 6A and 6B, another preferred embodiment of a stent graft 210 is shown that includes a tubular prosthetic graft (not shown for clarity) attached to a support structure 216. A biosensor 212 is attached to the stent graft 210 by a pair of filaments 218 that are attached at predetermined locations on the stent graft 210, preferably at adjacent locations such that the filaments 218 extend at least partially around a circumference of the stent graft 210.

As the stent graft 210 is expanded from its reduced profile to its enlarged profile, the biosensor 212 may be positioned immediately adjacent an outer surface of the stent graft 210 at a desired location along the length and/or around the circumference of the stent graft 210. Thus, the filaments 218 may have predetermined lengths that allow the biosensor 212 to be positioned adjacent the stent graft 210 on a delivery device 130, yet still place the biosensor 212 at a predetermined location within a cavity 58 across which the stent graft 210 is implanted.

Delivery of the stent graft 210 follows a similar method to that described above. The stent graft 210 is mounted on a distal region 138 of a catheter 132 with the biosensor 212 placed within a cavity 146 defined by a tapered nose portion 144. A sheath 136 is advanced over the stent graft 210 until it engages the tapered nose portion 144, a tongue 146 extending from the sheath 136 holding the biosensor 212 within the tapered nose portion 144.

The delivery device 130 may then be introduced into a patient, advanced to a target treatment site 50, and the sheath 136 withdrawn to expose the stent graft 210. The stent graft 210 may be expanded, either automatically or using a balloon, to its enlarged profile, thereby engaging the healthy regions 54, 56 of the treatment site 50 and substantially isolating a cavity 58 defined by a weakened region 52 from the rest of the vessel. The delivery device 130 may then be withdrawn, leaving the stent graft 210 implanted across the weakened region 52, with the biosensor 212 deployed within the cavity 58.

While the invention is susceptible to various modifications, and alternative forms, specific examples thereof have been shown in the drawings and are herein described in detail. It should be understood, however, that the invention is not to be limited to the particular forms or methods disclosed; but to the contrary, cover all modifications, equivalents and within the spirit and scope of the appended

What is claimed is:

1. A stent graft, comprising:
   a tubular prosthetic graft comprising an outer surface;
   a support structure expandable between a contracted condition for facilitating introduction into a blood vessel, and an enlarged condition for securing the graft across a weakened region of the blood vessel; and an acoustic biosensor attached to at least one of the graft and the expandable support structure, the acoustic biosensor comprising means for converting acoustic energy received from an externally originated signal into a current supply for powering a pressure sensor embedded in the acoustic biosensor, the pressure sensor having at least a portion exposed to a region external to the stent graft to sense pressure beyond the outer surface of the graft within the weakened region of the blood vessel when the graft is secured within the blood vessel.

2. The stent graft of claim 1, wherein the acoustic biosensor is directly attached to an outer surface of the graft such that the pressure sensor is exposed outside the graft.

3. The stent graft of claim 2, wherein the acoustic biosensor is attached to the graft by sutures or an adhesive.

4. The stent graft of claim 1, wherein the acoustic biosensor is directly attached to struts comprising the support structure.

5. The stent graft of claim 1, wherein the support structure comprises a self-expanding stent.

6. The stent graft of claim 1, wherein the support structure comprises a balloon-expandable stent.

7. The stent graft of claim 1, wherein the weakened region of the blood vessel comprises an aneurysmal sac, and the acoustic biosensor is configured for sensing a pressure within the aneurysmal sac when the graft is secured within the blood vessel.

8. The apparatus of claim 4, wherein the support structure is attached to an inner surface of the graft, and wherein the acoustic biosensor is mounted in a hole through the graft such that the pressure sensor is exposed outside the graft.

* * * * *